United States Patent [19]

Geigert et al.

[11] Patent Number: 4,503,153
[45] Date of Patent: Mar. 5, 1985

[54] METHOD FOR PRODUCING ALDEHYDES FROM PRIMARY ALCOHOLS

[75] Inventors: John Geigert, Clayton; Saul L. Neidleman, Oakland, both of Calif.

[73] Assignee: Cetus Corporation, Emeryville, Calif.

[21] Appl. No.: 570,790

[22] Filed: Jan. 16, 1984

Related U.S. Application Data

[63] Continuation of Ser. No. 362,746, Mar. 29, 1982, abandoned.

[51] Int. Cl.³ .............................................. C12P 7/24
[52] U.S. Cl. .................................... 435/147; 435/254; 435/911
[58] Field of Search ............... 435/161, 147, 253, 254, 435/822, 911

[56] References Cited

U.S. PATENT DOCUMENTS

| | | | |
|---|---|---|---|
| 3,880,739 | 4/1975 | Leavitt | 195/28 R |
| 4,218,401 | 8/1980 | Wymore | 567/402 |
| 4,220,803 | 9/1980 | Marcinkowsky et al. | 562/538 |
| 4,224,254 | 9/1980 | Sauer et al. | 568/431 |
| 4,241,184 | 12/1980 | Hou et al. | 435/138 |
| 4,246,347 | 1/1981 | Neidleman et al. | 435/105 |
| 4,247,641 | 1/1981 | Neidleman et al. | 435/123 |
| 4,353,987 | 10/1982 | Wolf | 435/147 |

OTHER PUBLICATIONS

R. Couderc et al., Agric. Biol. Chem. 44, 2279-2289 (1980).
J. A. Thomas et al., J. Biol. Chem. 245, 3129-3134 (1970).
Cooney, C. L. & Hueter, J., "Enzyme Catalysis in the Presence of Nonaqueous Solvents Using Chloroperoxidase", *Biotech. & Bioengi.*, XVI:1045-1053 (1974).
Morris, D. R. & Hager, L. P., "Chloroperoxidase", *J. Biol. Chem.*, 241, No. 8:1763-1768 (1966).
Pickard, M., *Can. J. Microbiol.* 27, 1298-1305 (1981).
J. A. Thomas et al., J. Biol. Chem., 245, 3135-3142 (1970).

*Primary Examiner*—R. B. Penland
*Attorney, Agent, or Firm*—Albert P. Halluin; Elliott L. Fineman; Janet E. Hasak

[57] ABSTRACT

A method is described for the manufacture of aldehydes from primary alcohols by enzymatic reaction. The aldehydes are produced by contacting a primary alcohol with a reaction mixture consisting of chloroperoxidase and hydrogen peroxide.

8 Claims, No Drawings

METHOD FOR PRODUCING ALDEHYDES FROM PRIMARY ALCOHOLS

This is a continuation of application Ser. No. 362,746, filed Mar. 29, 1982, abandoned.

This invention relates generally to an enzymatic process for making useful commercial products from primary alcohols. More particularly, the invention relates to an improved process for the production of aldehydes from primary alcohols wherein an enzyme is used to effect the reaction.

The industrial utility of aldehydes is well known. Aldehydes are used as intermediates for the manufacture of solvents, resins, dyes and polymers. They also find use in the perfume and flavoring industry.

Aldehydes are presently produced by several methods including the dehydrogenation of primary alcohols in the presence of certain well known oxidizing catalysts:

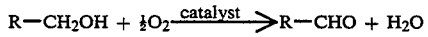

However, when these catalysts are employed, overoxidation leading to the corresponding acid (R—CO₂H) is a common problem (U.S. Pat. No. 4,220,803, Marcinkowsky et al., 1980). Also, oxidation of secondary alcohols (leading to ketones) can occur along with, and even in preference to oxidation of primary alcohols (U.S. Pat. No. 4,218,401, Wymore, 1980). It is also pointed out that benzyl alcohols (R=C₆H₅) are difficult to dehydrogenate, forming ethers easily (U.S. Pat. No. 4,224,254, Sauer et al., 1980). Moreover, these oxidizing catalysts require elevated temperatures (150°–500° C.).

In comparison to the conventional catalytic dehydrogenation processes, the process of the invention gives a better overall result with respect to purity of the product produced. Also, the process of the invention requires ambient temperature for operation, resulting in a major thermal energy savings.

Aldehydes are also produced by the dehydrogenation of primary alcohols in the presence of certain well known oxidase enzymes:

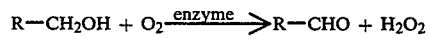

However, when these enzymes are employed, expensive co-factors such as NADH and/or NADPH are consumed during the production. Also, oxidation of secondary alcohols (leading to ketones) can occur along with, and even in preference to oxidation of primary alcohols (U.S. Pat. No. 4,241,184, Hou et al., 1980). Moreover, co-product must be either consumed or decomposed to prevent H₂O₂ inactivation of the oxidase enzyme (Couderc et al, Agric. Biol. Chem. 44, 2279 (1980)).

In comparison to the conventional enzymatic dehydrogenation processes, the process of the invention requires no expensive co-factor. Instead, the process of the invention involves the use of dilute H₂O₂, not necessarily purified. The H₂O₂ may be added directly or generated in situ by an enzymatic or chemical reaction. This reduces the cost of the H₂O₂ as compared to the cost of concentrated, purified material; it also increases the safe usage of the substance and extends the life of the enzyme.

Accordingly, it is an object of the present invention to provide a process for preparing aldehydes from primary alcohols.

It is also an object of the present invention to prepare aldehydes from primary alcohols in the presence of secondary alcohols.

It is a further object of the present invention to provide a low cost process for producing aldehydes from primary alcohols.

Other objects will become apparent to those skilled in the art from the following description.

Very generally, the method of the invention produces aldehydes from primary alcohols by providing in a reaction vessel a mixture of a primary alcohol and hydrogen peroxide. Chloroperoxidase is then introduced into the vessel and maintained in contact with the reaction mixture for a sufficient period of time to convert the primary alcohol to the desired aldehyde. The aldehyde is then recovered.

The present invention is based on the discovery that chloroperoxidase from *Caldariomyces fumago* (ATCC 16373) acts upon certain classes of primary alcohols to produce aldehydes. The preferred primary alcohols are the allylic (C=C—CH₂OH), propargylic (C≡C—CH₂OH) and benzylic (φ—CH₂OH) primary alcohols.

In the past, it was noted that chloroperoxidase could oxidize ethanol (a saturated primary alcohol) to acetaldehyde (an aldehyde):

(Thomas et al, J. Biol. Chem. 245, 3129 and 3135 (1970)). However, it has not heretofore been obvious that other classes of primary alcohols would be suitable, or even preferred, for reaction with chloroperoxidase. For example, both catalase and chloroperoxidase can oxidize primary alcohols in the presence of H₂O₂. But the reaction of the preferred primary alcohols of this invention is completely opposite to what one would expect from these two enzymes: for example, catalase is much more reactive toward ethanol (CH₃—CH₂OH) than toward allyl alcohol (CH₂=CH—CH₂OH), but as the present invention discloses, chloroperoxidase is much more reactive toward allyl alcohol than toward ethanol. Therefore, it was not obvious that chloroperoxidase would prefer the allylic, propargylic and benzylic primary alcohols. Also, it has not heretofore been obvious that only certain classes of primary alcohols, not secondary nor tertiary alcohols, would be oxidized by chloroperoxidase.

The term "primary alcohol" as used in connection with the present invention is represented by the following structural formula: R—CH₂OH, wherein R is a hydrocarbon.

Representative primary alcohols are: R—CH₂OH

| Primary Alcohol | R |
|---|---|
| allyl alcohol | CH₂=CH |
| crotyl alcohol | CH₃CH=CH |
| 3-buten-1-ol | CH₂=CHCH₂ |
| cinnamyl alcohol | φCH=CH |
| 2-butene-1,4-diol | HOCH₂CH=CH |
| propargyl alcohol | CH≡C |
| 2-butyne-1,4-diol | HOCH₂C≡C |
| benzyl alcohol | φ |
| phenethyl alcohol | φCH₂ |

| Primary Alcohol | R |
|---|---|
| Furfuryl alcohol | 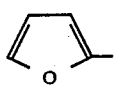 |
| 2-pyridyl carbinol | 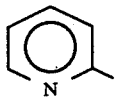 |
| m-methyl benzyl alcohol | 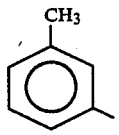 |

The present invention makes use of a haloperoxidase enzyme. Chloroperoxidase derived from the microorganism *Caldariomyces fumago* (ATCC 16373) is the haloperoxidase capable of carrying out the method of the present invention. Bromoperoxidase derived from algae, lactoperoxidase derived from milk, and horseradishperoxidase derived from horseradish are not capable of carrying out the method of the present invention.

The microorganism, *Caldariomyces fumago* (ATCC 16373), or a mutant microorganism having chloroperoxidase activity like that of chloroperoxidase from *Caldariomyces fumago* (ATCC 16373) may be grown as a static or agitated, submerged culture in Czapek-Dox medium at room temperature for 3 to 10 days by conventional methods. The enzyme, chloroperoxidase, is prepared from aqueous homogenate of the mycelial pads of microorganism grown under static conditions or from the filtrate of the microorganism grown under static or agitated submerged culture conditions. Detailed descriptions for preparing chloroperoxidase can be found in the following articles and patent: (1) U.S. Pat. No. 4,247,641 issued to Neidleman et al, on Jan. 27, 1981; (2) Morris et al, *J. Biol. Chem.* 241, 1763 (1966); and (3) Cooney et al, Biotech. Bioeng. 16, 1045 (1974).

The enzyme may also be used in an immobilized form. Processes for enzyme immobilization are familiar to those skilled in the art, and include reacting either a solution of the enzyme or a suspension of enzyme containing cells with one of a broad range of organic or inorganic supports. Included among these are polyacrylamide, ethylene-maleic acid copolymers, methacylic-based polymers, polypeptides, styrene-based polymers, agarose, cellulose, dextran, porous glass beads, and aluminum or titanium hydroxide. Enzymes in this form have increased stability, extended life and usefulness, and recoverability. Reactions employing immobilized enzymes may be run in columns or reaction tanks.

In addition to the enzyme, an oxidizing agent is required in the reaction mixture. A preferred oxidizing agent, hydrogen peroxide, is added directly to the mixture in a single batch addition, or in a continuous slow feed. It is alternatively generated as slow feed in situ by the use of a hydrogen peroxide-producing enzyme system. Such enzyme systems are well known in the art, and include glucose-1-oxidase in the presence of D-glucose, pyranose-2-oxidase in the presence of D-glucose, and D and L-amino acid oxidases in the presence of D- and L-methionine, and diamine oxidases in the presence of histamine. The hydrogen peroxide-generating system is present in the nonimmobilized state or immobilized state as is the haloperoxidase enzyme. The hydrogen peroxide can also be generated by a chemical reaction such as the anthraquinone oxidation process.

The hydrogen peroxide is present preferably in molar ratio of from about 0.5:1 to about 50:1, most preferably in a ratio of about 1:1 or less with respect to the primary alcohol. The molar ratio preferences refer to the average presence of hydrogen peroxide during the reaction. The actual molar ratio usually varies during the reaction and at any particular time may be above or below the ranges cited.

The reaction is conducted with a pH range of from about 2.8 to about 7.0. The pH of the reaction is preferably maintained within the desired range by use of a buffering agent. Suitable buffers include sodium or potassium phosphate, citrate, and acetate based systems. Other suitable techniques besides buffering may also be used for pH control and adjustment.

The reaction is conducted in an aqueous medium. While some of the primary alcohols that can be converted by the process are substantially insoluble in an aqueous medium, the reaction, nevertheless, occurs satisfactorily under conditions of mixing, or other modes of dispersion, which provide sufficient substrate solubility for the reaction.

The reaction is preferably conducted in the temperature range of about 15° C. to about 50° C., preferably at about 20° C. to about 30° C.

As previously indicated, the components of the reaction mixture, namely the primary alcohol, chloroperoxidase, hydrogen peroxide, and the buffering agent, are simply mixed together in water, agitated for a period of, for example, from about 30 seconds to about 1 hour to obtain the aldehyde.

The reaction for primary alcohols is represented by the following equation:

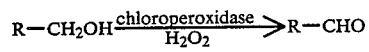

The products obtained by such reactions according to the present invention were identified and quantitated by gas chromatography-mass spectrometry (GCMS). Ten (10) μl of the reaction mixture was injected into a Finnigan 4021 GCMS, equipped with a 6 foot×4 mm coiled, glass column packed with Tenax-GC (80/100 mesh). Flow rate through the column was set at 30 ml/minute of helium. The column temperature was operated isothermally (specific temperature given in each example); the injection temperature was set at 240° C.; and the jet separator was set at 240° C. The mass spectrometer was operated at 70 eV, electron impact ionization.

The following examples are intended to further illustrate the invention and are not intended to limit the scope of the invention in any way.

EXAMPLE 1

This example illustrates the process for preparing aldehydes from primary alcohols.

Potassium phosphate buffer at pH 3.0 and pH 7.0 (10 ml, 0.3 M), hydrogen peroxide (4.1 mg; 137 μl of a 3% solution; 12 mM final) and benzyl alcohol (13 mg; 12 mM final; φCH$_2$OH; purchased from Aldrich Chemical Company, Milwaukee, WI) were mixed together in a 25 ml Pyrex flask at room temperature and room pressure. The haloperoxidase enzyme, chloroperoxidase (0.1 ml) was then added. The reaction was concluded 15 minutes after the addition of the last reagent.

The chloroperoxidase was prepared as follows:

Mycelial pads of *Caldariomyces fumago* (ATCC 16373) were grown on potato agar slants. Sliced potato (200 g) was cooked in distilled water (500 ml) for 40 minutes and then strained. A solution of glucose (21 g) and agar (20 g) in distilled water (500 ml) was added to the strained solution. The pH was adjusted to 6.8 and the volume was brought to 1 liter with distilled water. The medium was sterilized at 121° C. for 15 minutes.

The organism was inoculated on the potato agar slants, produced in accordance with the above procedure, and was grown for about one week at room temperature. The organism was then used to inoculate a soybean-glucose medium (50 ml). The soybean-glucose medium was prepared by adding, to 1 liter of distilled water, extraction process soybean meal (30 g), glucose (30 g), and $CaCO_3$ (7 g). The medium was sterilized at 121° C. for 30 minutes and was then inoculated with the organism after cooling.

The organism was grown for 4–5 days on a rotary shaker at 25° C. Five ml of this material was used to inoculate a 500 ml Erlenmeyer flask containing 100 ml of a modified Czapek-Dox medium prepared by adding the following to 1 liter of distilled water: $NaNO_3$ (3 g), $KH_2PO_4$ (1 g), KCl (0.5 g), $MgSO_4 \cdot 7H_2O$ (0.5 g), $FeSO_4 \cdot 7H_2O$ (10 mg), and glucose (40 g). The medium was sterilized at 121° C. for 20 minutes prior to inoculation with the organism.

The organism was grown under static conditions at room temperature for 5–7 days. The black mycelial pads which formed were collected, rinsed with distilled water, and stored in plastic bags in a freezer at −10° C. for subsequent use.

The halogenating enzyme was prepared by grinding 6 mycelial pads (prepared in accordance with the above procedures) with a 60 g acid-washed sand and 60 ml of distilled water for 2 minutes in Virtis 45 homogenizer. The homogenate was centrifuged while cold and the supernatant solution was used as the source of the halogenating enzyme, chloroperoxidase.

The final chloroperoxidase supernatant was filtered through Whatman No. 1 paper at room temperature. The filtrate was concentrated about 10-fold using a rotary film evaporator at reduced pressure and temperature (<35° C.). The concentrate was chilled at 0° C. in an ice bath, and pre-chilled (0° C.) ethanol was added until 45% ethanol (v/v) was reached. The mixture was stirred vigorously for 15 minutes, and then centrifuged at −10° C. (at 15,000 g) with a 55-34 rotor in a Sorval RC-5 Superspeed for 15 minutes. The black sediment was discarded. To the centrifugate, cooled at 0° C., was added additional prechilled ethanol to give 65% ethanol (v/v). The mixture was slowly stirred for 30 minutes at 0° C., and then centrifuged as before. The centrifugate was discarded, and the precipitate containing the chloroperoxidase activity was dissolved in 1 ml of 0.05 M potassium phosphate (pH 7). The enzyme solution was stored at −20° C.

The product was identified and quantitated by gas chromatography-mass spectrometry (GCMS). 10 μl of the reaction mixture was injected into a Finnigan 4021 GCMS, equipped with a 6 foot×4 mm coiled glass column packed with Tenax-GC (80/100) mesh. Flow rate through the column was set at 30 ml/minute of helium. The column temperature was 200° C.; and the jet separator was set at 230° C. The mass spectrometer was operated at 70 eV, electron impact ionization.

The product had a GC retention time of 8 minutes and showed the mass spectrum diagnostic for benzaldehyde: molecular mass ion at mass 106; major fragment mass ions at mass 105 (loss of H from molecular ion), and at mass 77 (the $\phi^{30}$ ion). This product had an identical GC retention time and mass spectrum with that of an authentic sample of benzaldehyde (purchased from Aldrich Chemical Company).

| The following summarizes the product yields obtained: | | |
| --- | --- | --- |
| | Yield | |
| Product | At pH 3 | At pH 7 |
| $\phi$CHO | 6.1 mg | 5.6 mg |

EXAMPLE 2

This example illustrates that the allylic, propargylic and benzylic primary alcohols are the preferred primary alcohols for use in the method of this invention.

The procedure of Example 1 was followed except the buffer pH was set at pH 5. The following primary alcohols were run (12 mM final; all purchased from Aldrich Chemical Company) and these results obtained:

| PRIMARY ALCOHOL SUBSTRATE | | ALDEHYDE PRODUCT | | YIELD |
| --- | --- | --- | --- | --- |
| $CH_3CH_2OH$ | ethanol | $CH_3CHO$ | acetaldehyde | 0.1 mg |
| $CH_3CH=CHCH_2OH$ | crotyl alcohol | $CH_3CH=CHCHO$ | crotonaldehyde | 2.3 |
| $\phi CH=CHCH_2OH$ | cinnamyl alcohol | $\phi CH=CHCHO$ | cinnamaldehyde | 5.2 |
| $CH_2=CHCH_2CH_2OH$ | 3-buten-1-ol | $CH_2=CHCH_2CHO$ | 3-buten-1-al | 0.3 |
| $HOCH_2CH=CHCH_2OH$ | 2-butene-1,4-diol | $HOCH_2CH=CHCHO$ | 4-hydroxy-2-buten-1-al | 3.6 |
| $HC\equiv CH_2OH$ | propargyl alcohol | $HC\equiv CCHO$ | propargyl aldehyde | 1.3 |
| $HOCH_2C\equiv CCH_2OH$ | 2-butyne-1,4-diol | $HOCH_2C\equiv CCHO$ | 4-hydroxy-2-butyn-1-al | 1.5 |
| $\phi CH_2CH_2OH$ | 2-phenethanol | $\phi CH_2CHO$ | phenylacetaldehyde | 2.2 |
| 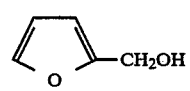 | furfuryl alcohol | 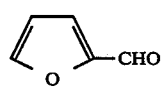 | furfural | 3.7 |
| 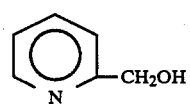 | 2-pyridyl carbinol | 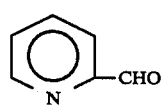 | 2-pyridyl aldehyde | 2.9 |

| PRIMARY ALCOHOL SUBSTRATE | | ALDEHYDE PRODUCT | | YIELD |
|---|---|---|---|---|
| CH₃-phenyl-CH₂OH | m-methyl benzyl alcohol | CH₃-phenyl-CHO | m-methylbenzaldehyde | 3.2 |

These products had identical GC retention times and mass spectra with that of authentic samples purchased from Aldrich Chemical Company.

EXAMPLE 3

This example illustrates the use of semi-continuous feed of hydrogen peroxide in the method of the present invention.

The procedure of Example 1 was followed, except four additions of 4.1 mg hydrogen peroxide (137 μl of a 3% solution added in each addition) were added 15 minutes apart. Allyl alcohol (7 mg, 12 mM final; $CH_2=CHCH_2OH$; purchased from Aldrich Chemical Company) was the primary alcohol added.

The product had a GC retention time of 2.9 minutes at a column temperature of 130° C., isothermal; and showed the mass spectrum diagnostic for acrolein: molecular mass ion at mass 56; major fragment mass ion at mass 55 (loss of H from molecular ion). This product had an identical GC retention time and mass spectrum with that of an authentic sample of acrolein (purchased from Aldrich Chemical Company.

The following summarizes the product yields obtained:

| Product | Total Yield | | | | Addition of $H_2O_2$ |
|---|---|---|---|---|---|
| | 1st | 2nd | 3rd | 4th | |
| $CH_2=CHCHO$ | 2.2 mg | 4.1 mg | 5.9 mg | 6.2 mg | |

EXAMPLE 4

The selective oxidation of primary alcohols in the presence of secondary alcohols is illustrated by this example. The procedure of Example 2 was followed except two alcohol substrates were added to the reaction mixture: a primary alcohol, 2-phenethanol ($\phi CH_2CH_2OH$; 12 mM final) and a secondary alcohol, 1-phenethanol ($\phi CH(OH)CH_3$; 12 mM final; purchased from Aldrich Chemical Company).

Only the primary alcohol (2-phenethanol) was oxidized.

The following summarizes the product yield obtained:

| Substrate | Product | Product Yield |
|---|---|---|
| $\phi CH_2CH_2OH$ | $\phi CH_2CHO$ | 2.2 mg |
| $\phi CHCH_3$ with OH | $\phi CCH_3$ with O | None detected |

EXAMPLE 5

Slow-feed in situ enzymatic generation of hydrogen peroxide is illustrated by this example.

The procedure of Example 1 was followed except: (1) the potassium phosphate buffer was set a pH 6.0, (2) the hydrogen peroxide was generated by in situ enzymatic generation. To the reaction mixtures, β-D-glucose (10 mM final) and either glucose-1-oxidase (0.1 ml; purchased from Sigma Chemical Company; Catalog G-6500) or pyranose-2-oxidase (0.1 ml; prepared according to U.S. Pat. No. 4,246,347) were added. The reaction was concluded 60 minutes after the oxidase enzyme was added.

The following summarizes the product yields obtained:

| | Yield | |
|---|---|---|
| Product | With glucose-1-oxidase | With pyranose-2-oxidase |
| $\phi CHO$ | 8.0 mg | 6.1 mg |

The oxidized product of glucose using glucose-1-oxidase was D-glucono-δ-lactone and using pyranose-2-oxidase was D-glucosone.

Thus it can be seen that the invention discloses a method for producing aldehydes from primary alcohols by enzymatic reaction. The enzyme utilized in disclosed method in chloroperoxidase from the microorganism *Caldariomyces fumago* (ATCC 16373). It can be used free or in immobilized form. The primary alcohols used in making the aldehydes are preferably the allylic, propargylic and benzylic primary alcohols.

Unlike known enzymatic dehydrogenation processes, the method of the present invention requires no expensive co-factor. In addition, because the method is run at ambient temperature it results in major thermal energy savings when compared to the present conventional methods. The method also makes possible the selective oxidation of primary alcohols in the presence of secondary alcohols.

Various modifications of the invention in addition to those shown and described herein will become apparent to those skilled in the art from the foregoing description. Such modifications are intended to fall within the scope of the appended claims.

What is claimed is:

1. A method of making an aldehyde of formula $R_1CHO$ from a primary alcohol of formula $R_1CH_2OH$, wherein $R_1$ is selected from the group consisting of
   (i) $R_2CH=CH(CH_2)_n-$,
   (ii) $R_2C\equiv C(CH_2)_n-$, and
   (iii) $R_3(CH_2)_n-$,
wherein n is 0 or 1; $R_2$ is hydrogen, methyl, ethyl, n-propyl, isopropyl, hydroxymethyl, hydroxyethyl or $R_4$; $R_3$ is 2-pyridyl, 3-pyridyl, 4-pyridyl, 2-furyl, 3-furyl or $R_4$; and $R_4$ is phenyl optionally substituted at any one position with methyl; provided that, if $R_2$ is hydroxymethyl, n is 0, which comprises reacting, in an aqueous medium, chloroperoxidase from *Caldariomyces fumago* with the primary alcohol in the presence of an oxidizing agent at ambient temperature and pressure and with a pH range of about 3 to about 7, until the primary alcohol is converted to the corresponding aldehyde.

2. A method in accordance with claim 1 wherein the oxidizing agent is hydrogen peroxide.

3. A method in accordance with claim 1 wherein the primary alcohol is selectively oxidized in the presence of a secondary alcohol.

4. A method in accordance with claim 1 wherein the primary alcohol is selected from the group consisting of: allyl alcohol, crotyl alcohol, 2-butyne-1,4-diol, cinnamyl alcohol, 2-butene-1,4-diol, 3-buten-1-ol, propargyl alcohol, benzyl alcohol, phenethyl alcohol, furfuryl alcohol, 2-pyridyl carbinol, and m-methylbenzyl alcohol.

5. A method in accordance with claim 14 wherein the oxidizing agent is hydrogen peroxide.

6. A method in accordance with claim 5 wherein the primary alcohol is allyl alcohol.

7. A method in accordance with claim 5 wherein the primary alcohol is benzyl alcohol.

8. A method in accordance with claim 5 wherein the primary alcohol is propargyl alcohol.

* * * * *